US00PP35512P2

(12) United States Plant Patent
Spil

(10) Patent No.: US PP35,512 P2
(45) Date of Patent: Nov. 28, 2023

(54) ***ECHINACEA* PLANT NAMED 'IFECSSCAR'**

(50) Latin Name: *Echinacea hybrida*
Varietal Denomination: IFECSSCAR

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 18/118,419

(22) Filed: Mar. 7, 2023

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./263.1, 428
See application file for complete search history.

(56) References Cited

U.S. PATENT DOCUMENTS

PP34,082 P2 * 3/2022 van Noort ..... A01H 6/1448 Plt./428

* cited by examiner

*Primary Examiner* — Karen M Redden
(74) *Attorney, Agent, or Firm* — C. Anne Whealy

(57) ABSTRACT

A new and distinct cultivar of *Echinacea* plant named 'IFECSSCAR', characterized by its relatively compact and upright plant habit; moderately vigorous to vigorous growth habit; freely branching habit; strong flowering stems; numerous single-type inflorescences with purplish red-colored ray florets and dark red-colored receptacle spines; and good garden perfotmance.

2 Drawing Sheets

Figure 1:
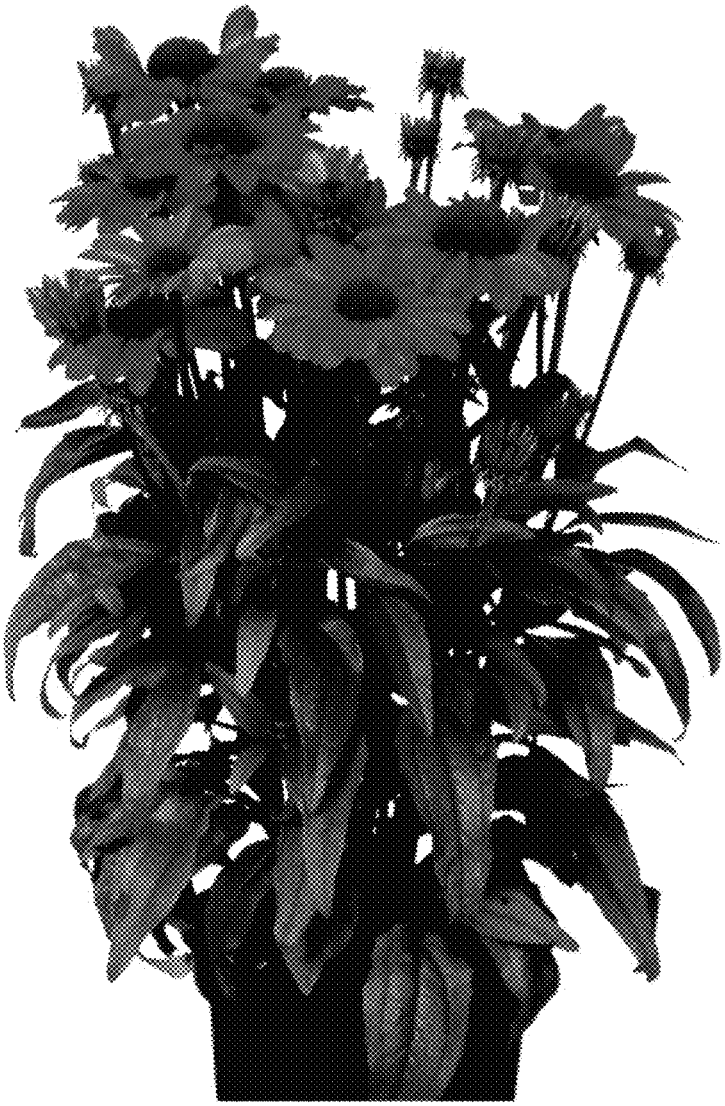

Botanical designation: *Echinacea hybrida.*
Cultivar denomination: 'IFECSSCAR'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Innoflora Plant Breeding B.V. of Heerhugowaard, The Netherlands on Nov. 24, 2022, application number 2022/2654. Foreign priority is not claimed to this application.

BACKGROUND OF THE INVENTION

The present invention relates to a new and distinct cultivar of *Echinacea* plant, botanically known as *Echinacea hybrida*, and hereinafter referred to by the name 'IFECSSCAR'.

The new *Echinacea* plant is a product of a planned breeding program conducted by the Inventor in Heerhugowaard, The Netherlands. The objective of the breeding program is to develop new vigorous and freely flowering *Echinacea* plants with large inflorescences with unique and attractive ray floret coloration.

The new *Echinacea* plant originated from a cross-pollination conducted by the Inventor in July, 2018 in Heerhugowaard, The Netherlands of *Echinacea hybrida* 'Apecssired', disclosed in U.S. Plant Pat. No. 28,825, as the female, or seed, parent with a proprietary selection of *Echinacea hybrida* identified as code number 009-17-K061-01, not patented, as the male, or pollen, parent. The new *Echinacea* plant was discovered and selected by the Inventor as a single flowering plant from within the progeny of the stated cross-pollination grown in a controlled greenhouse environment in Heerhugowaard, The Netherlands in August, 2019.

Asexual reproduction of the new *Echinacea* plant by in vitro meristem culture in a controlled environment in Heerhugowaard, The Netherlands since September, 2019 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'IFECSSCAR'. These characteristics in combination distinguish 'IFECSSCAR' as a new and distinct *Echinacea* plant:

1. Relatively compact and upright plant habit.
2. Moderately vigorous to vigorous growth habit.
3. Freely branching habit.
4. Strong flowering stems.
5. Numerous single-type inflorescences with purplish red-colored ray florets and dark red-colored receptacle spines.
6. Good garden performance.

Plants of the new *Echinacea* can be compared to plants of the female parent, 'Apecssired'. Plants of the new *Echinacea* differ primarily from plants of 'Apecssired' in the following characteristics:

1. Plants of the new *Echinacea* are shorter than plants of 'Apecssired'.
2. Plants of the new *Echinacea* are not as freely flowering as plants of 'Apecssired'.
3. Ray florets of plants of the new *Echinacea* are purplish red in color whereas ray florets of plants of 'Apecssired' are red in color.

Plants of the new *Echinacea* can be compared to plants of the male parent selection. Plants of the new *Echinacea* differ primarily from plants of the male parent selection in the following characteristics:

1. Plants of the new *Echinacea* are taller than plants of the male parent selection.
2. Inflorescences of plants of the new *Echinacea* have two whorls of ray florets whereas inflorescences of plants of the male parent selection have a single whorl of ray florets.
3. Ray florets of plants of the new *Echinacea* are purplish red in color whereas ray florets of plants of the male parent selection are pink in color.

Plants of the new *Echinacea* can be compared to plants of *Echinacea* hybrid 'Sensation Pink', disclosed in U.S. Plant Pat. No. 26,593. In side-by-side comparisons, plants of the new *Echinacea* differ primarily from plants of 'Sensation Pink' in the following characteristics:

1. Plants of the new *Echinacea* are more compact than plants of 'Sensation Pink'.
2. Plants of the new *Echinacea* have stronger stems than plants of 'Sensation Pink'.
3. Plants of the new *Echinacea* are not as freely flowering as plants of 'Sensation Pink'.
4. Inflorescences of plants of the new *Echinacea* have two whorls of ray florets whereas inflorescences of plants of 'Sensation Pink' have a single whorl of ray florets.
5. Ray florets of plants of the new *Echinacea* are purplish red in color whereas ray florets of plants of 'Sensation Pink' are bright pink in color.

Plants of the new *Echinacea* can also be compared to plants of *Echinacea purpurea* 'Fatal Attraction', disclosed in U.S. Plant Patent number 18,429. In side-by-side comparisons, plants of the new *Echinacea* differ primarily from plants of 'Fatal Attraction' in the following characteristics:

1. Plants of the new *Echinacea* are more compact than plants of 'Fatal Attraction'.
2. Plants of the new *Echinacea* flower earlier than plants of 'Fatal Attraction'.
3. Ray florets of plants of the new *Echinacea* are purplish red in color whereas ray florets of plants of 'Fatal Attraction' are red purple in color.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet (FIG. 1) is a side perspective view of a typical flowering plant of 'IFECSSCAR' grown in a container.

Figure 2:
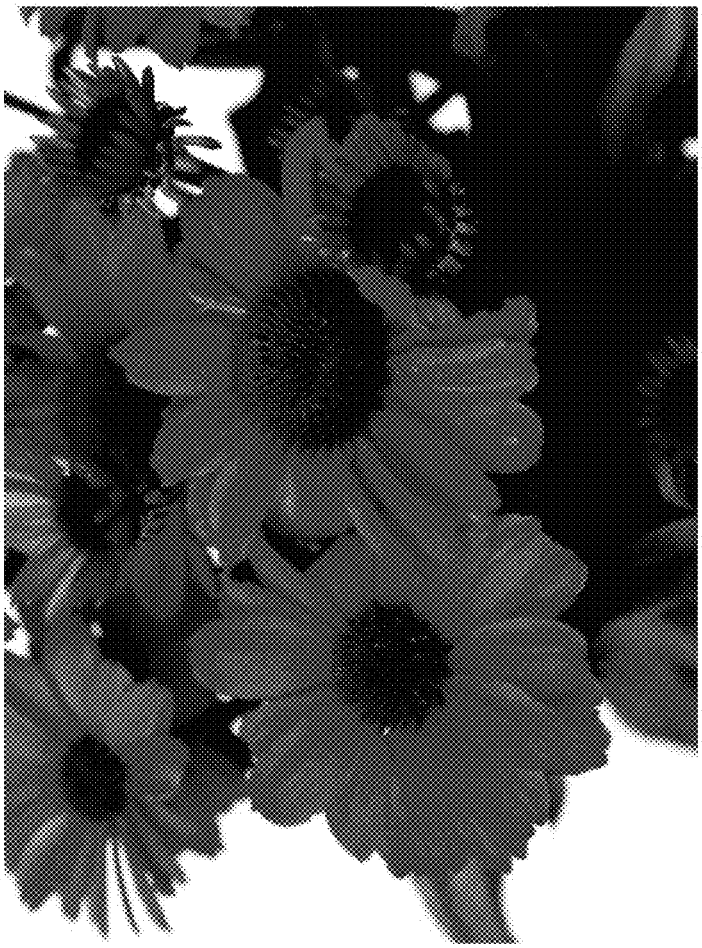

The photograph at the left of the second sheet (FIG. 2) is a close-up view of typical inflorescences of 'IFECSSCAR'.

Figure 3:
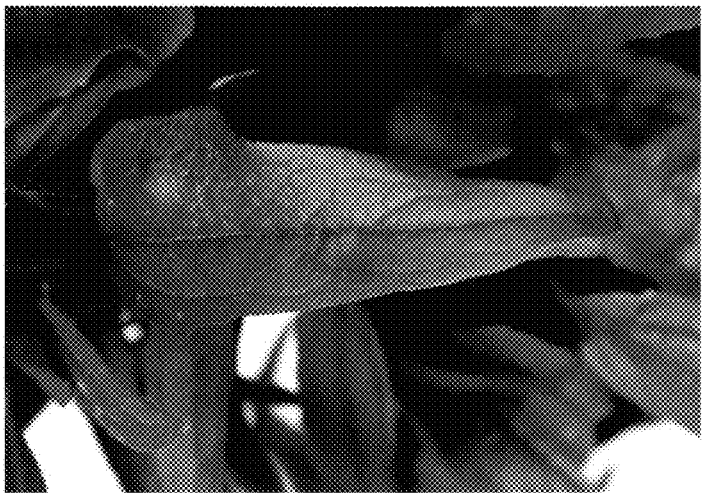

The photograph at the right of the second sheet (FIG. 3) is a close-up view of typical leaves of 'IFECSSCAR'.

DETAILED BOTANICAL DESCRIPTION

The aforementioned photographs and following observations and measurements describe plants grown during the summer in 19-cm containers in an outdoor nursery in Heerhugowaard, The Netherlands and under cultural practices typically used in commercial *Echinacea* production. During the production of the plants, day temperatures ranged from 18C to 34C and night temperatures ranged from 8C to 18C. Plants were 15 weeks old when the photographs and description were taken. In the following description, color references are made to The Royal Horticultural Society Colour Chart, 2015 Edition, except where general terms of ordinary dictionary significance are used.

Botanical classification: *Echinacea hybrida* 'IFECSSCAR'.

Parentage:

*Female parent.*—*Echinacea hybrida* 'Apecssired', disclosed in U.S. Plant Pat. No. 28,825.

*Male parent.*—Proprietary selection of *Echinacea hybrida* identified as code number 009-17-K061-01, not patented.

Propagation:

*Type.*—By in vitro meristem culture.

*Time to initiate roots, summer.*—About twelve days at temperatures about 20C.

*Time to initiate roots, winter.*—About 16 days at temperatures about 20C.

*Time to produce a rooted young plant, summer.*—About 36 days at temperatures about 18C.

*Time to produce a rooted young plant, winter.*—About 42 days at temperatures about 18C.

*Root description.*—Thick, fleshy; typically white in color, actual color of the roots is dependent on substrate composition, water quality, fertilizer type and formulation, substrate temperature and physiological age of roots.

*Rooting habit.*—Moderately freely branching; sparse.

Plant description:

*Plant form and growth habit.*—Herbaceous perennial; relatively compact and upright plant habit; broadly oblong to obovate in overall shape; freely basal branching habit with about eleven primary lateral branches and about 14 secondary lateral branches developing per plant; moderately vigorous to vigorous growth habit and moderate growth rate.

*Plant height.*—About 45.8 cm.

*Plant diameter or spread.*—About 38.3 cm.

*Lateral branches.*—Length: About 20.7 cm. Diameter: About 6 mm. Internode length: About 4.1 cm. Aspect: Erect to about 12.5 degrees from vertical. Strength: Strong. Texture: Densely pubescent; strigose. Color: Close to 200B to 200D; on the shaded side, tinged with close to 152C.

Leaf description:

*Basal and cauline leaves.*—Arrangement: Alternate, simple. Length: About 13.7 cm. Width: About 5 cm. Shape: Ovate to narrowly ovate. Apex: Narrowly acute; moderately recurved. Base: Attenuate. Margin: Irregular, shallow and broadly dentate. Texture and luster, upper surface: Moderately pubescent, strigose and rough; slightly glossy. Texture and luster, lower surface: Sparsely pubescent, strigose and rough; slightly glossy. Venation pattern: Pinnate. Color: Developing leaves, upper surface: Slightly darker than 143A. Developing leaves, lower surface: Close to 144A. Fully expanded leaves, upper surface: Close to NN137A; venation, close to 146B to 146C. Fully expanded leaves, lower surface: Close to 137B; venation, close to 146C and 146D.

*Petioles, basal and cauline leaves.*—Length: About 5.7 cm. Diameter: About 3 mm by 4 mm. Texture, upper surface: Smooth, glabrous. Texture, lower surface: Sparsely pubescent. Color, upper surface: Close to 137A; midvein, close to 146D variably tinged with close to 183B. Color, lower surface: Close to 137B; midvein, close to 146D slightly tinged with close to 183C.

Inflorescence description:

*Appearance.*—Single-type inflorescences with ray and disc florets arranged on a capitulum; inflorescences positioned upright above the foliar plane on mostly upright and strong peduncles.

*Flowering habit.*—Freely flowering habit with about 36 developing and fully developed inflorescences per plant.

*Fragrance.*—If detected, faintly fragrant; sweet and pleasant.

*Time to flower.*—Plants flower continuously from late June into late September in The Netherlands.

*Inflorescence longevity.*—Inflorescences maintain good substance for about three weeks on the plant; inflorescences persistent.

*Inflorescence buds.*—Height: About 3 cm. Diameter: About 2.9 cm. Shape: Obovate. Color: Immature involucral bracts, close to 137A; immature ray florets, close to 187D; immature receptacle spines, darker than a blend of 187A and 200A.

*Inflorescence size*—Diameter: About 10.4 cm. Depth (height): About 3.4 cm. Disc diameter: About 3.2 cm.

*Receptacles.*—Height: About 1.1 cm. Diameter: About 9 mm. Shape: Broadly ovate. Color: Close to 155C.

*Ray florets.*—Quantity and arrangement: About 27 to 30 arranged in about two whorls at the base of the receptacle. Length: About 4.6 cm. Width: About 1.8 cm. Shape: Oblong to broadly oblanceolate; slightly carinate. Apex: Praemorse, irregular. Base: Cuneate. Margin: Entire. Texture and luster, upper surface: Smooth, glabrous; moderately velvety; matte. Texture and luster, lower surface: Smooth, glabrous; slightly glossy. Aspect: Erect to about 20 degrees from horizontal; with development, apices slightly curled downward. Color: When opening, upper surface: Close to a blend of 51A and 53D. When opening, lower surface: Close to 58A. Fully opened, upper surface: Close to 60B; venation, close to 60B; color becoming closer to 60C to 60D with subsequent development. Fully opened, lower surface: Close to 60C and 63B; venation, close to 60C and 63B; color becoming closer to 60B and 63C with subsequent development.

*Disc florets.*—Quantity and arrangement: About 280 per inflorescence, arranged spirally at the center of the inflorescence. Length: About 1.1 cm. Diameter: About 3 mm. Shape: Tubular; proximal 11% free, not fused. Apex: Acute. Base: Fused. Margin, free-part: Entire. Texture and luster, inner and outer surfaces: Smooth, glabrous; moderately glossy. Color, when opening, inner and outer surfaces: Distally, close to 183A and proximally, close to 146D. Color, fully opened, inner and outer surfaces: Distally, close to 183A and proximally, close to 146D.

*Receptacle spines.*—Quantity: One per disc floret; about 280 per inflorescence. Shape: Acicular. Apex: Acute. Base: Attenuate. Texture and luster: Smooth, glabrous; glossy. Color: Apex: Close to N45A. Midsection: Close to N34B. Base: Close to 145A.

*Involucral bracts.*—Quantity per inflorescence: About 80 arranged in about four whorls. Length: About 1.2 cm. Width: About 3 mm. Shape: Narrowly ovate; strongly reflexed. Apex: Acute. Base: Cuneate. Margin: Entire. Texture and luster, upper surface: Smooth, glabrous; slightly glossy. Texture and luster, lower surface: Sparsely pubescent; matte. Color, upper surface: Close to 147A strongly tinged with close to 183A. Color, lower surface: Close to 146A.

*Peduncles.*—Length: About 16.8 cm. Diameter: About 5 cm. Strength: Strong. Aspect: Mostly upright. Texture: Moderately to densely pubescent; strigose. Color: Close to 187A; distally, tinged with close to 146A.

*Reproductive organs.*—Androecium (present on ray and disc florets): Quantity per floret: Five. Filament length: About 4 mm. Filament color: Close to 150D. Anther length: About 3.5 mm. Anther shape: Linear. Anther color: Close to N200A. Pollen amount: Moderate. Pollen color: Close to 17B. Gynoecium (present only on disc florets): Quantity per floret: One. Pistil length: About 6 mm. Stigma shape: Decurrent, unequal. Stigma color: Close to 183A. Style length: About 5 mm. Style color: Close to 145D. Ovary color: Close to 157C.

*Seeds and fruits.*—To date, seed and fruit development have not been observed on plants of the new *Echinacea*.

Pathogen & pest resistance: To date, plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35C and to be hardy to USDA Hardiness Zones 3 to 4.

It is claimed:

1. A new and distinct *Echinacea* plant named 'IFECSSCAR' as illustrated and described.

* * * * *